(12) United States Patent
Schuler et al.

(10) Patent No.: US 12,115,048 B2
(45) Date of Patent: Oct. 15, 2024

(54) DEVICE FOR SHAPING TAMPONS

(71) Applicant: Ruggli AG, Koblenz (CH)

(72) Inventors: Samuel Schuler, Basel (CH); Marco Auer, Waldshut-Tiengen (DE)

(73) Assignee: Ruggli AG, Koblenz (CH)

( * ) Notice: Subject to any disclaimer, the term of this patent is extended or adjusted under 35 U.S.C. 154(b) by 1052 days.

(21) Appl. No.: 17/042,318

(22) PCT Filed: Mar. 20, 2019

(86) PCT No.: PCT/IB2019/052261
§ 371 (c)(1),
(2) Date: Sep. 28, 2020

(87) PCT Pub. No.: WO2019/186325
PCT Pub. Date: Oct. 3, 2019

(65) Prior Publication Data
US 2021/0077308 A1    Mar. 18, 2021

(30) Foreign Application Priority Data

Mar. 29, 2018 (CH) .......................... 426/18

(51) Int. Cl.
*A61F 13/20* (2006.01)
(52) U.S. Cl.
CPC ................ *A61F 13/2088* (2013.01)
(58) Field of Classification Search
CPC ............. A61F 13/2088; A61F 13/2085; A61F 13/2082–13/2097; B65G 29/00
USPC ................................... 28/118–120
See application file for complete search history.

(56) References Cited

U.S. PATENT DOCUMENTS

| 2,566,190 | A | | 8/1951 | Greiner et al. | |
| 3,131,435 | A | * | 5/1964 | Henry | A61F 13/2085 28/119 |
| 4,113,083 | A | * | 9/1978 | Friese | B65G 47/846 198/803.15 |
| 5,084,038 | A | * | 1/1992 | Sheldon | A61F 13/2082 156/193 |
| 2005/0022349 | A1 | * | 2/2005 | Pham | A61F 13/2085 28/118 |
| 2005/0236256 | A1 | * | 10/2005 | Draghetti | B65G 47/08 198/418 |

(Continued)

FOREIGN PATENT DOCUMENTS

| DE | 3505457 C2 * | 6/1995 | ............. A24C 5/322 |
| EP | 2 412 351 A1 | 2/2012 | |

OTHER PUBLICATIONS

International Search Report in PCT/IB2019/052261, mailed Jun. 24, 2019.

*Primary Examiner* — Amy Vanatta
(74) *Attorney, Agent, or Firm* — Collard & Roe, P.C.

(57) ABSTRACT

The present invention relates to an apparatus for forming tampons, which comprises a plurality of processing drums 2, 4, 5.1, 5.2 for forming a tampon from band-form material. It also comprises at least one transfer station 7 for continuously transferring a preform from a first processing drum 2, 4, 5.1, 5.2 to a second processing drum 4, 5.1, 5.2. The invention also relates to a method for forming a tampon from band-form material, wherein transfer from a first processing drum to a second processing drum takes place by means of a continuously rotating transfer wheel.

16 Claims, 6 Drawing Sheets

(56) References Cited

U.S. PATENT DOCUMENTS

| | | | |
|---|---|---|---|
| 2012/0071839 A1* | 3/2012 | Wada | A61F 13/2074 604/286 |
| 2012/0086140 A1* | 4/2012 | Hosokawa | A61F 13/28 264/129 |
| 2012/0089074 A1* | 4/2012 | Wada | A61F 13/2074 604/385.18 |
| 2013/0036584 A1* | 2/2013 | Ishikawa | A61F 13/2085 28/118 |
| 2019/0015263 A1* | 1/2019 | Cankar | B65H 69/04 |
| 2022/0280348 A1* | 9/2022 | Heege | A61F 13/2082 |

* cited by examiner

DEVICE FOR SHAPING TAMPONS

CROSS REFERENCE TO RELATED APPLICATIONS

This application is the National Stage of PCT/IB2019/052261 filed on Mar. 20, 2019, which claims priority under 35 U.S.C. § 119 of Switzerland Application No. 00426/18 filed on Mar. 29, 2018, the disclosure of which is incorporated by reference. The international application under PCT article 21(2) was not published in English.

The present invention relates to an apparatus for forming tampons from band-form material, and to a method for forming a tampon from band-form material, both according to the preamble of the characterizing claims.

TECHNOLOGICAL BACKGROUND

Tampons that are used for feminine hygiene, in particular during menstruation, consist primarily of an absorbent material, usually a viscose-cotton strip, which is initially wound into the characteristic elongate shape and is then compressed and formed. These operations of processing the band-form starting material into the finished tampon are carried out incrementally on cycled production lines. In a first step, first of all the strip of material is wound, wherein a retrieval thread is placed around the strip and is knotted prior to winding. Subsequently, the coil is compressed under pressure. As a result of an appropriate design of the pressing tool, it is possible to create particular structures on the finished tampon, for example the common longitudinal slots. In most production methods, in order to obtain a particularly smooth and round tampon head, a head forming step is additionally carried out, which additionally forms and/or smooths the tampon head. Each of these processing steps takes place at a specialized workstation and requires cycled transfer from one workstation to the next.

As a result of the cycle of this transfer, limits are imposed on a tampon production line as regards the possible maximum speed that is achievable. The constant acceleration and deceleration of the operating units also results in heavy wear and high energy consumption.

Particular attention also needs to be paid, in tampon production, to the sensitivity of the processed materials, since the cotton, or the cotton/nonwoven band, has to be transported with appropriate care so as to avoid any loss of quality in the end product. A further aggravating factor is the highly hygroscopic property of the material, wherein the air humidity has to be kept in a narrow range, since only an optimum material moisture content ensures that the process proceeds reliably.

Therefore, there is a need for apparatuses and methods for forming tampons, which can reach a high process speed without accepting drawbacks in the quality of the products produced.

Here, in the production of tampons, the speed is measured in the number of processed workpieces per minute. In the current art, these piece numbers are between 100 and 140 items per minute at most, but actually often lie therebeneath.

SUMMARY OF THE INVENTION

Therefore, it is an object of the present invention to provide an apparatus for producing tampons, which overcomes at least one of the abovementioned problems. In particular, an apparatus for producing tampons is intended to be produced which can reach piece numbers of more than 140 items per minute. Correspondingly, a method is also intended to be provided, which overcomes at least one of the drawbacks of the known art, and in particular can process piece numbers of over 140 items per minute.

This object is achieved by an apparatus for forming tampons, as described in the characterizing part of the independent claims.

Therefore, one aspect of the present invention relates to an apparatus for forming tampons from a band-form material. This apparatus comprises a plurality of processing drums and at least one transfer station, in particular a transfer wheel, for continuously transferring a preform from a first processing drum to a second processing drum. In this way, a continuously operable apparatus for producing tampons or preforms is provided.

For the present invention, the starting point is a band-form material, which may already have been subjected to prior processing steps. Thus, for tampon production, use is made in particular of band-form materials which consist of laminated sheets of woven and/or nonwoven materials. Commonly, a nonwoven/cotton material is used. For the invention, the specific composition of these band-form materials is of secondary importance.

Within the meaning of the present invention, a tampon can be understood to be any type of cotton stick pressed to form a substantially elongate object, which serves mainly to be introduced into a body orifice or a wound.

The forming comprises, within the meaning of the invention, the steps required to make just such a tampon from the band-form material, in particular a tampon that has a head shape that narrows substantially at a head end and has an elongate body. Such tampons are generally used by women as hygiene products during menstruation. However, tampons that are provided for other purposes can be produced equally well using the apparatus according to the invention. Thus, it is also possible for anal tampons or haemostatic tampons for use in surgery to be produced with the apparatus according to the invention without or with only minor adaptations. Such tampons can be designed for example without a narrowing head.

Downstream of the apparatus according to the invention there may be further processing steps, for example the packaging of the tampons in a film or an applicator. In one particular embodiment, the packaging of the tampons in a film or an applicator can be carried out by components according to the invention, for example by processing drums. In a further particular embodiment, a packaging drum is provided for packaging.

CA 2085923, for example, shows a method by way of which a band-form material, which would be suitable for the apparatus of the present invention, can be prepared.

Within the meaning of the present invention, a processing drum can be understood to be a drum that is mounted so as to be rotatable about a central axis and has radially arranged processing tools for a specific forming step in tampon forming. The processing drum can be directly driven; in particular each processing drum can be directly driven separately.

Within the meaning of the present invention, a transfer station can be understood to be a station that is positionable between the processing drums and has radially circumferentially arranged receiving grippers for the continuous transfer of a workpiece. For this purpose, it is possible to provide for example endless belts or chains, in particular chain belts, which have circumferentially arranged receiving grippers, in particular which comprise a plurality of receiving grippers along a profile of the outer circumference of a belt. With such transfer stations, the workpieces can be transferred in a constant and continuous manner.

In one particular embodiment, the transfer station is a transfer wheel having radially circumferentially arranged receiving grippers, which describe a substantially circular radius upon rotation about the axis of rotation of the transfer wheel.

In one particular embodiment, the apparatus according to the invention comprises at least one first and at least one second processing drum. A first processing drum can be designed to wind the fed band-form material into a coil. The second processing drum can be provided to compress said coil.

Within the meaning of the present invention, the term preform is used for a precursor product of a tampon, which has undergone at least one processing step. Thus, within the meaning of the present invention, the wound band-form material can be considered to be the first preform. If this coil, or preform, is pressed, the resulting product can already be a tampon, or, if it is processed by further steps, it can become a second preform, which can in turn be processed further to form a tampon or possibly even a third preform. Thus, it is possible, for example after compression, to provide further quality-enhancing processing steps, which are carried out on the preforms.

In one particular embodiment, the present invention comprises a third processing drum, which carries out head forming and/or smoothing of the second preform.

In a further particular embodiment, the apparatus according to the invention comprises a fourth processing drum, which is designed to smooth the tampon head or the tampon surface.

In one particular embodiment, the processing drums are arranged in succession on a production line, such that each process step is passed through in a particular order by the preforms. Particularly preferably, between each pair of adjacent processing drums, a respective transfer station is arranged, which is responsible for transferring the preforms between the processing drums.

The transfer station is arranged in the apparatus according to the invention such that the transfer of a preform from a first processing drum to a second processing drum is continuous. Preferably, the transfer station is a transfer wheel.

Previous methods and apparatuses for producing and forming tampons proceed discontinuously overall, because at least one transfer between the processing wheels takes place via an intermittently operating transfer unit. With the apparatus according to the invention, it is possible to produce tampons in large piece numbers per minute in a continuous endless method.

Since the transfer takes place via a transfer wheel, the maintenance requirement is also reduced, given that less wear occurs on the components that operate otherwise in a stop-and-go method. Machine operation is smoother overall and the wear is reduced.

A further advantage of the apparatus according to the invention is that the continuously proceeding process is scalable. Thus, it is possible for example to increase the number of tools on the processing drums, with the result that it is possible to optimize the use of space in manufacturing plants. Although manufacturing plants with more tools per processing drum can turn out to be more bulky, the increased space requirement is less than if several production lines are set up in parallel. The scalability makes it possible to develop production lines that are tailored to customer requirements and have a desired number of processing tools per processing drum. At the same time, the processing duration on the workpiece can be kept constant for the individual processing tools. Any differences in the number and/or processing speed between two adjacent processing drums can be compensated for by the continuously working transfer stations, or transfer wheels.

For certain applications, it may be appropriate to reduce the piece number below the maximum possible ejection number. This may be useful for example in control or calibration processes of the apparatuses, but also in order to accommodate corresponding postprocessing machines. This too is rendered possible by the stepless scalability of the continuously operating transfer wheel. In spite of the high possible process speed and piece numbers, more time can thus remain for the individual process steps as a result of the apparatus according to the invention. Thus, it is possible, for example, for the workpiece to remain in the tool throughout the residence time on a processing drum and at the same time is transported in the conveying direction. A plurality of tools per processing drum allow higher piece numbers, without at the same time reducing the processing time per workpiece. It is thus possible, for example, for the processing drum configured for pressing to have a plurality of processing tools, i.e. presses, preferably six presses, which can each process the workpiece for a period of time from receiving the workpiece from a transfer wheel up to the transfer to a further transfer wheel. The radially next roller meanwhile takes the next workpiece.

In one particular embodiment, the processing drum comprises at least two radially arranged processing tools. Preferably, the processing tools are arranged such that centrifugal forces that arise during operation are balanced at the outer radius of the processing drums, i.e. the processing tools are arranged symmetrically to one another about the central axis of rotation.

In one particular embodiment, a processing drum comprises between six and 24 processing tools.

A further advantage of the present invention is disclosed here. As a result of the steplessly operable and continuously working transfer wheels, it is possible nevertheless to allow a continuous feed of workpieces between two processing drums with different numbers of processing tools.

In one particular embodiment, each transfer wheel of the apparatus according to the invention is controllable separately.

In one particular embodiment, the processing drums are configured such that, while they rotate about their drum axis, they process the workpiece or the preform and transport same in a conveying direction of the apparatus. In other words, the processing by the processing drum can also be configured preferably to be continuous.

In one particular embodiment, the transfer wheel comprises a plurality of receiving grippers. These receiving grippers are designed such that they engage in a transfer region at a rotation radius of at least one of the processing drums. During operation, the processing drums rotate about their drum axis, such that an outer radius is formed, at which the processing tools are arranged on the processing drum. Preferably, in the present apparatus, a processing drum and a transfer wheel are arranged with respect to one another such that a transfer region arises. From this transfer region, a transfer wheel can pick up a corresponding preform or workpiece fully processed by the processing drum and transfer it to the next processing drum.

In one particular embodiment, the transfer wheel comprises at least one guide curve. This guide curve can guide the receiving gripper in a radial movement such that, during a rotation of the transfer wheel relative to a first processing drum, a transfer region is defined, in which a receiving nest of a receiving gripper is substantially coaxial with a processing tool of a processing drum.

Within the meaning of the present invention, the receiving nest and the processing tool are coaxial with one another when they are arranged coaxially with regard to their longitudinal axis. This longitudinal axis can also correspond to the longitudinal axis of the workpiece in the processing tool or receiving nest.

In one particular embodiment of the present invention, the transfer wheel has radially arranged receiving grippers. These receiving grippers comprise a receiving nest for receiving a tampon or a preform. They also comprise a guide rod on which the receiving nest is arranged. In addition, the receiving gripper according to the invention comprises a guide bushing by way of which the guide rod is mounted so as to be displaceable along its longitudinal axis. This guide bushing can in turn be fastened to a rotatable hub.

In one particular embodiment, the guide bushing is mounted on the rotatable hub so as to be pivotable about an axis of rotation. For example, the guide bushing can be mounted in a pivotable manner with respect to the hub by means of a radial bearing. Preferably, this axis of rotation is parallel to the axis of rotation of the transfer wheel, i.e. is embodied at right angles to the longitudinal axis of the guide rod. One advantage of this arrangement is that, for the receiving grippers, the tangential speed thereof can be corrected along their guide curves.

In addition to a longitudinal displacement of the guide rod along the bearing of the guide bushing, the entire receiving gripper is pivotable about an axis of rotation. This allows a further degree of freedom and makes it possible to adapt the turning speed of the receiving nest to the turning speed of the tool of the processing drum in the transfer region. The receiving nest can travel along the guide curve at a non-constant speed in the transfer region.

In one particular embodiment, the guide rod also comprises a first engagement means for operative connection to a first guide curve. In operation, during the rotation of the hub, the transfer wheel is rotated parallel to a first rigidly arranged guide curve, which acts as a guide element for the individual receiving grippers. The receiving grippers can be operatively connected to the guide curve by means of an engagement means in the form of a peg or cam. Thus, the receiving grippers do not just move in rotation about the axis of rotation of the transfer wheel but also, during this movement, travel along a curve which is defined by the guide curve. As a result, it is possible, in the transfer region to a processing drum, to engage in the latter and to pass into a coaxial position with a tool of the processing drum, wherein, for a particular time, there is a substantially identical turning speed, such that a workpiece can be transferred from the tool into the receiving nest of the receiving gripper.

In one particular embodiment, the receiving gripper comprises a second engagement means for operative connection to a second guide curve. During the rotation of the hub, the transfer wheel is rotated parallel to the second rigidly arranged guide curve, which serves as a guide element for the guide bushing.

The receiving gripper is preferably configured such that the receiving nest has at least two degrees of freedom. A first degree of freedom is achieved by mounting the guide rod at its longitudinal axis on the guide bushing. A further degree of freedom is achieved by the guide bushing being rotatably mounted on the hub.

In one particular embodiment, the first guide curve and the second guide curve are arranged parallel to one another, in particular arranged as slots in two parallel guide discs. The slots can follow different curve paths. Between the two parallel guide discs with the guide curves, the receiving grippers are arranged in a manner mounted rotatably on the hub. The receiving grippers have a first cam for operatively connecting to the first guide curve, and a second cam for operatively connecting to the second guide curve. The cams are arranged opposite one another on the receiving grippers in this embodiment, but are preferably not arranged concentrically.

As a result of this arrangement, the receiving gripper is guided in its radial movement along a curve such that, at least for a while, in a transfer region, it has the same turning speed as a radially arranged tool of a processing drum.

In one particular embodiment, the transfer wheel is configured as a drum, wherein the receiving grippers are arranged on a hub arranged rotatably between two rigid guide discs.

In one particular embodiment, the processing drums comprise an ejection drum, which is arranged parallel to the processing drum and is arranged so as to be rotatable about the same axis as the associated processing drum.

In one particular embodiment, the ejection drum comprises a plurality of ejection push rods that are arranged at a radius of the ejection drum such that they are arranged parallel to the processing tools of the associated processing drum.

In a further preferred embodiment, the ejection push rods are arranged on the ejection drum such that they extend substantially coaxially with the tools. In this embodiment, during the transfer from the processing drum to the transfer wheel or vice versa, a coaxial arrangement of the ejection push rod of an ejection drum, of the tool of the associated processing drum, and of the receiving nest of the transfer wheel will occur in the transfer region.

In a further particular embodiment, the ejection drum comprises a three-dimensional guide element, along which the ejection push rods are guided. The guide element can be arranged such that the ejection push rods act in the intermediate space between the ejection drum and the processing drum when there is coaxial arrangement with a receiving nest of the transfer wheel. In this way, it is possible for example for the transfer of a workpiece or preform from a transfer wheel into a corresponding processing tool to be ensured.

In one particular embodiment, the guide curve is in the form of a slot, in which a peg or pin of a receiving gripper can engage such that, during a movement of the receiving gripper about the axis of rotation of the transfer wheel, the guide rod is displaced along the guide bushing in the longitudinal direction.

As an alternative to a guide curve, the receiving grippers can also be embodied in an actuated manner. In this case, electric, pneumatic or hydraulic actuators would allow a movement of the guide rod in a radial direction with regard to the transfer wheel. Corresponding additional actuators could be provided in order to allow a pivoting movement of the transfer gripper.

In a further alternative embodiment, the receiving grippers can also be mounted in a resilient manner. In one particular embodiment of this variant, a processing drum comprises means for entering into an operative connection with the receiving grippers at least in a transfer region of its radius. Thus, it is possible to provide for example hooks on the processing drum, which enter into an operative connection with corresponding eyes of the receiving grippers. This contact can be maintained for the duration of a workpiece transfer, for example by an ejection push rod. Alternatives or complements to the hooks and eyes would be magnetic carriers, which may be switched on and off electrically, or carriers operated by drawing in air. Within the meaning of the present invention, a receiving gripper can be mounted in a resilient manner in that a spring is arranged so as to be able to exert a restoring force in a radial direction on a receiving nest.

In one particular embodiment, the ejection drums are additionally equipped, at the location of the ejection push rods, with suction devices which maintain an air flow in the direction of the tools of the processing drum. This serves to control withdrawal threads of the tampons in the processing region, preventing tangling of the tampon threads. For this purpose, the receiving nests can also be provided with a receiving slot, which makes it possible for the receiving nests, upon engagement in the receiving region, not to come into contact with withdrawal threads projecting horizontally into the transfer region by way of a corresponding suction element of the ejection drum. Corresponding suction elements can also be provided on the transfer wheels, specifically in a corresponding manner for each receiving nest, in order to prevent tangling of the withdrawal threads during the transfer.

In one particular embodiment, the first processing drum is a winding drum. Preferably, the winding drum has between six and 24, particularly preferably twelve tools.

In one particular embodiment, in this case, the second processing drum is a processing drum having a plurality of tampon presses, preferably between two and twelve tampon presses, particularly preferably six tampon presses. Tampon presses, which are designed to exert pressure on a coil radially via a plurality of pressing jaws and thus to compress said coil to form a tampon, are known in the prior art.

In one particular embodiment, all components that are in physical contact with the band-form material, a preform or the tampon, have an antistatic coating or consist substantially of an antistatic material.

In one particular embodiment, the apparatus comprises drives for the transfer stations, in particular transfer wheels and processing drums.

A further aspect of the present invention relates to a method for forming a tampon from band-form material. In a first step, a band-form material is provided. In this case, the band-form material, as outlined at the beginning, may have already been pre-processed and in common cases is a laminate made of a nonwoven and absorbent cotton. The band-form material is formed incrementally via a plurality of rotating processing drums. Preferably, these are continuously rotating processing drums. In the process, transfer from a first processing drum to a second processing drum takes place continuously by means of a transfer station, in particular by means of a transfer wheel.

As a result of the method according to the invention, the piece-number output of an apparatus for forming tampons is dissociated from the processing time of the individual workpiece. In spite of the high possible piece numbers, no losses have to be accepted during processing times of the individual workpieces. This allows production with a high output, with simultaneously very high quality.

In one particular embodiment of the method according to the invention, the incremental forming of the band-form material comprises a winding step, a pressing step and a head forming and/or smoothing step. In this case, each of the steps takes place on a particular, continuously rotating processing drum.

In one particular embodiment, the processing drums move the workpiece or the preform onward in a conveying direction in each incremental forming step.

In one particular embodiment, during the transfer from a first processing drum to a second processing drum, the transfer station or the transfer wheel executes the step of engaging with a receiving gripper in a transfer region of a first processing drum, such that a receiving nest of the receiving gripper is located at least for a while in a coaxial arrangement with a tool. An ejecting drum executes the step of ejecting a workpiece from the tool into the receiving nest, or from the receiving nest into the tool, in particular by displacing an ejection push rod in the longitudinal direction of the tool or receiving nest.

Within the meaning of the present invention, a coaxial arrangement of the tool, of the receiving nest and of the ejection push rod always means in relation to the longitudinal extent of the corresponding elements. This also corresponds to the longitudinal extent of the tampons produced using the method according to the invention, or of the tampons formed with the apparatus according to the invention.

In one particular embodiment, in the second step, the ejection push rod is arranged on an ejection drum, which rotates parallel to the corresponding processing drum, such that the ejection push rods are each assigned to a corresponding tool.

In a further particular embodiment of the method according to the invention, a receiving gripper of the transfer wheel is guided, during rotation of the latter, over a guide curve, such that there is the same speed in a transfer region between the processing drum and a receiving nest. Preferably, this identical speed is with respect to a tool of the processing drum.

For a person skilled in the art, it goes without saying that all embodiments of the present invention that are not mutually exclusive can be configured in any desired combination.

DESCRIPTION OF THE FIGURES

In the following text, the present invention will now be explained in more detail with reference to specific exemplary embodiments and schematic drawings, but without being limited to these particular embodiments.

For the sake of simplicity, in the present figures, identical components are provided with the same reference signs.

In the figures, in each case schematically:

FIG. 3a shows a basic design of an apparatus according to the present invention with two processing drums and a transfer wheel arranged in between;

EMBODIMENT OF THE INVENTION

Figure 1:
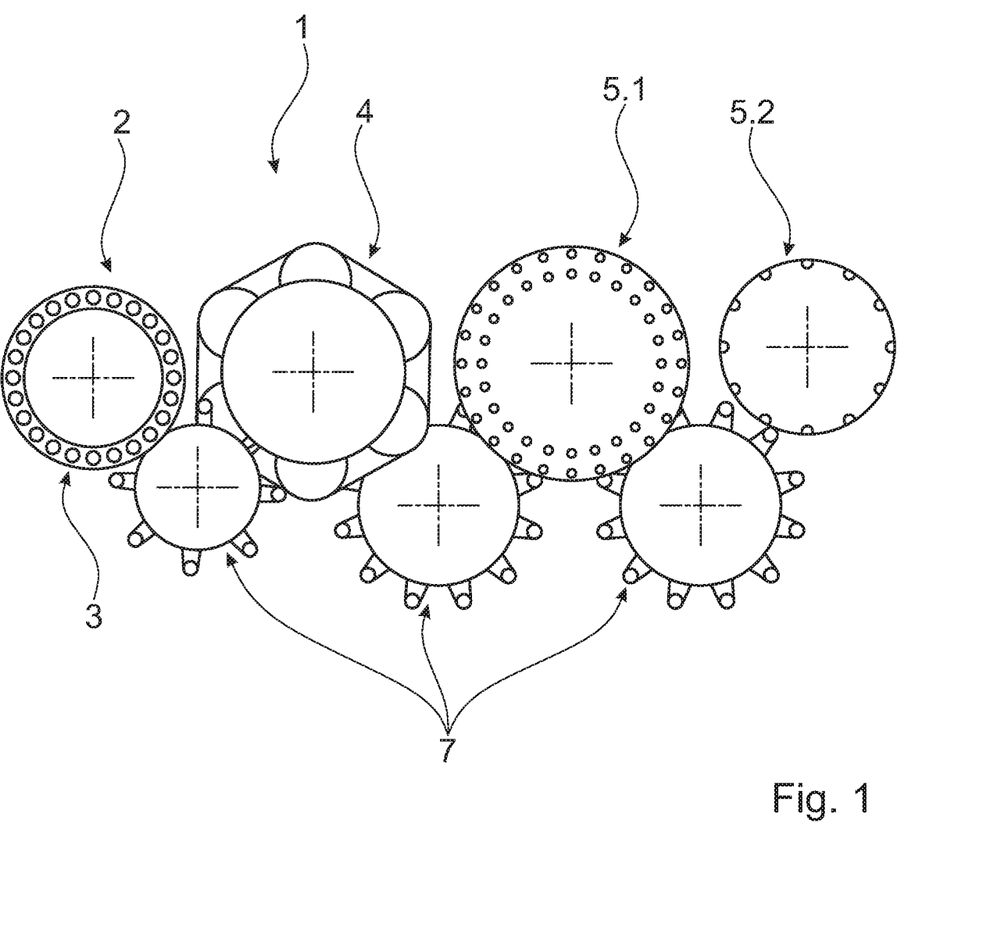
FIG. 1 shows an embodiment of the apparatus according to the invention with a total of four processing drums.

FIG. 1 schematically shows an apparatus 1 according to the invention with a total of four processing drums 2, 4, 5.1,

5.2. Although this example is illustrated with four drums 2, 4, 5.1, 5.2, the apparatus is already functional even with just two drums 2, 4. The processing drums 2, 4, 5.1, 5.2 are arranged in succession and each execute a processing step in the forming of tampons.

A first processing drum 2 serves as a winding station. The band-form material is introduced into the first processing drum 2 and is then wound by the first processing drum 2 to form coils and the first preform. In order to wind the band-form material, the first processing drum 2 can be equipped with a set of forks that take the band-form material and wind it into a coil by means of a rotary movement about their respective axes of rotation. The band-form material can, as outlined at the beginning, be a laminate made of a nonwoven and absorbent cotton. In this case, the absorbent cotton can originate from any cellulose fibre material, but is preferably made of viscose. Alternatively, cotton or hemp fibres are conceivable. The nonwoven comprises preferably a thermoplastic copolymer.

The apparatus 1 has a conveying direction. For the present example, the conveying direction is from left to right in FIG. 1. The workpieces travel in this conveying direction during operation.

Upstream processing stations that are not shown can produce the corresponding laminate and introduce the band-form material, already cut to the right size, into the first processing drum 2.

The first processing drum 2 is followed by a first transfer wheel 7. This transfer wheel takes the coil from the first processing drum 2 and transfers it to the second processing drum 4. In the present example, the first processing drum 2 is equipped such that it rotates in the clockwise direction about the horizontal axis of rotation. The tools, in particular winding forks, are arranged radially. The transfer wheel 7 is configured such that it rotates in the anticlockwise direction about a likewise horizontally extending axis of rotation.

The following second processing drum 4 is a drum for compressing the coils and preforms to form second preforms.

The second processing drum comprises a plurality of pressing tools. The pressing tools can be radially arranged pressing jaws. Overall, however, the number of pressing tools is lower than the number of winding tools of the first processing drum. The transfer wheel is capable of compensating for different speeds between two processing drums 2, 4, 5.1, 5.2. This can be ensured for example in that the transfer wheel comprises a corresponding guide, as shown in detail below.

The second processing drum 4 is followed by a third and a fourth processing drum 5.1, 5.2. The apparatus 1 according to the invention has two head forming/smoothing drums 5.1, 5.2. These drums are also each connected by a transfer wheel 7 to the preceding processing drum 4, which feeds the corresponding processing drum 5.1. Likewise, the transfer from the head forming drum 5.1 to the smoothing drum 5.2 takes place via a transfer wheel 7.

The transfer wheels 7 are configured such that they are rotatable continuously about their central axes of rotation. In the present example, the axes of rotation are oriented horizontally and indicated by the dashed crosses in FIG. 1. In the present exemplary embodiment, during operation, the transfer wheels rotate anticlockwise, while the processing drums 2, 4, 5.1, 5.2 rotate clockwise. Of course, the opposite structure is possible.

The entire arrangement can be mounted on a machine frame (not shown). Alternatively, workbenches, or mounting in a workroom are also conceivable. Also conceivable is integration into a fully automated production line with upstream and downstream processing.

Figure 2A:
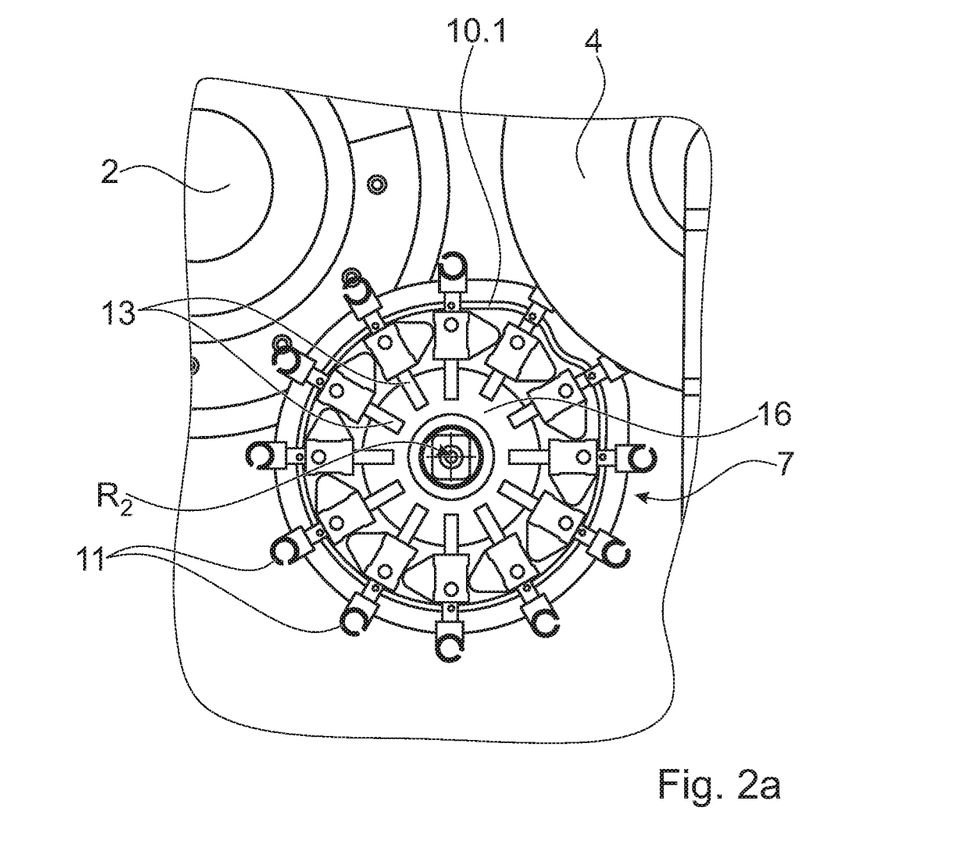
FIG. 2a shows a transfer wheel.

FIG. 2a schematically shows a transfer wheel 7 according to the invention in a detail view. The transfer wheel 7 is illustrated by way of example between two processing drums. The transfer wheel 7 is mounted so as to be rotatable about a central axis of rotation R2, which is oriented horizontally. In this case, a hub 16 rotates about the central axis of rotation R2. Connected to the hub 16 are the receiving grippers 12, which have radially displaceable guide rods 13, which are mounted in guide bushings. The guide rods 13 end in receiving nests 11, which are designed to receive a workpiece, in the present case a preform or a coil.

As is apparent in the figure, the processing drums are arranged in an offset manner with respect to one another along their axes of rotation, such that the transfer wheel 7 can act between the two processing drums 2, 4.

In order to compensate for the different speeds of the processing drums at the radii of the transfer wheels, a first guide curve 10.1, which is arranged rigidly with respect to the hub 16, is apparent in FIG. 2a.

The receiving grippers 12 are configured such that they are operatively connected to the first guide curve 10.1 and, during the rotation of the transfer wheel 7, follow the curve profile such that the guide rods 13, in addition to the radial rotation about the axis of rotation of the transfer wheel, can carry out a lateral pivoting movement and cranial displacement defined by the guide curve (with regard to the receiving nest as the head end). The receiving grippers 12 are guided by this first guide curve 10.1, as by a guide member.

Figure 2B:
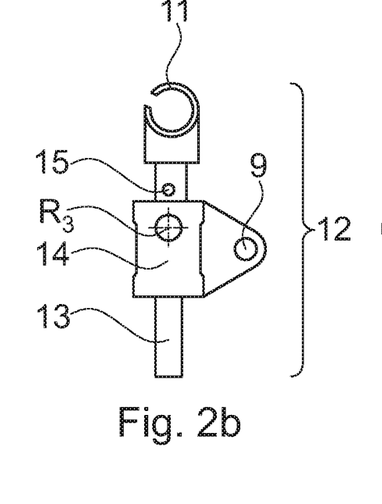
FIG. 2b shows a receiving gripper in a retracted state.
Figure 2C:
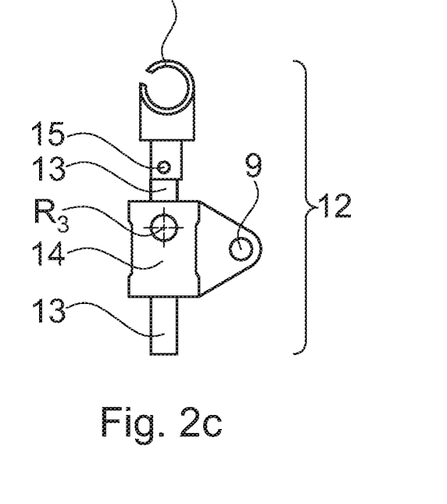
FIG. 2c shows a receiving gripper in an extended state.
Figure 2D:
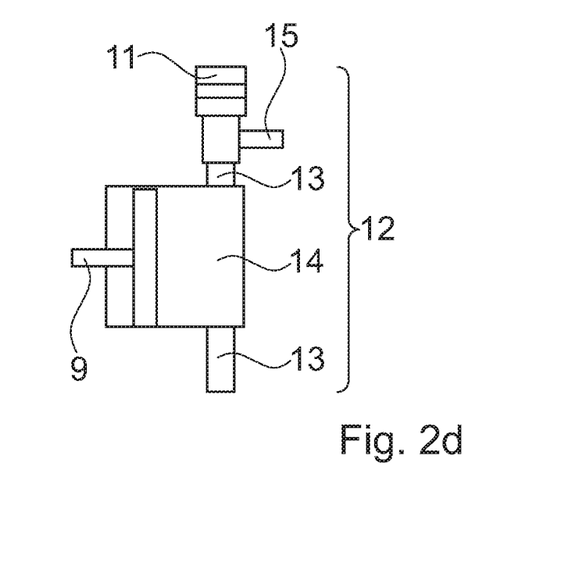
FIG. 2d shows the receiving gripper from FIG. 2c in side view.

In order to further explain the manner of operation of the receiving grippers 12 in the example according to the invention, one such receiving gripper 12 is also schematically illustrated on its own in FIGS. 2b, 2c and 2d.

The receiving gripper 12 comprises guided guide rods 13, which are mounted so as to be displaceable along their longitudinal axis by means of a guide bushing 14 having a linear bearing.

A first cam 15 is formed on the guide rod 13, in order to engage in a guide slot of the guide curve according to FIG. 2a. In the illustration in FIGS. 2b and 2c, this first cam 15 would extend in the plane of the paper facing away from the observer.

In the present example, the receiving gripper 12 is mounted so as to be rotatable about an axis of rotation R3 on the hub 16. This can be brought about by means of a radial bearing. In the present example, the radial bearing is formed by the hub and operatively connected to the guide bushing by a peg at the axis of rotation R3.

At the head side, the guide rod 13 ends with a receiving nest 11, which describes a lumen that serves to receive the workpiece. A lateral cutout serves, during positioning, to not touch the retrieval thread, projecting horizontally into a transfer region, during the transfer.

FIG. 2c shows a displacement of the mounted guide rod 13 along the longitudinal axis of the receiving gripper 12, as is allowed by a linear bearing of the guide bushing 14.

The guide bushing 14 has a second cam 9 on the plane of the paper facing the observer. This second cam 9 can be operatively connected to a second guide curve (this not being shown in FIG. 2a). This second guide curve serves as a guide member for guiding the guide bushing 14 along a curve. As a result, the receiving nest 11 can move in two degrees of freedom during a rotation of the transfer wheel 7, namely a longitudinal displacement in the longitudinal direction and a rotation about the axis of rotation R3. Since the two cams 9, 15 are arranged in an offset manner with respect to one another, the guidance by the two guide curves supports the radial movement of the receiving grippers on their curves.

FIG. 2*d* shows the receiving gripper 12 from FIG. 2*c* again, rotated through 90 degrees, in side view. The guide rod 13 has in this case been displaced slightly in a radial direction (with regard to the axis of rotation R2 of the transfer wheel; not shown in FIG. 2*d*). The guide bushing has the cam 9. The guide rod has the cam 15. At the receiving nest 11, in plan view, the lateral cutout is discernible.

Figure 3A:
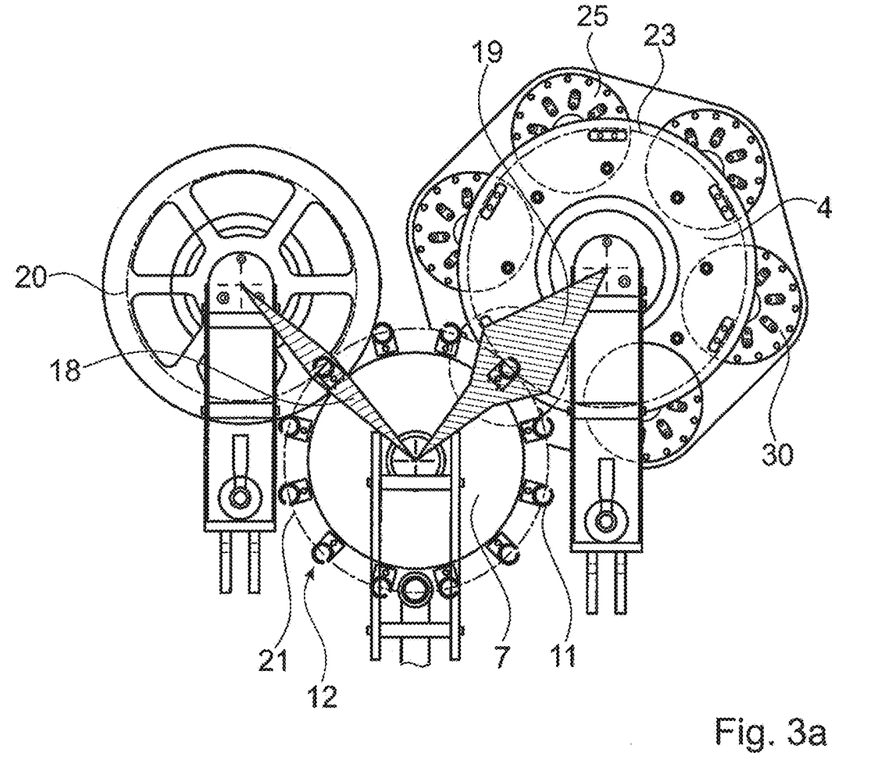

FIG. 3*a* shows an arrangement for better illustrating the transfer wheel 7 with two processing drums. A first processing drum describes, with the processing tools, a first radius 20, while a second processing drum 4 describes, with its tools, a second radius 23. In this case, these radii relate to the corresponding location of the workpiece in the tool. The second processing drum 4 is a processing drum 4 having a plurality of tampon presses 25, 30, which are arranged radially about the axis of rotation of the processing drum 4.

The axes of rotation of the processing drums 2, 4 are illustrated schematically by a central cross. Along these axes, a rotary shaft can be connected with rotary bearings to a rotary drive (this not being shown), wherein a direct drive of the individual processing drums, or an individual drive can drive both drums via a belt system.

The pressing tools 25, 30 are equipped with a plurality of radially arranged pressing tools, in particular with pressing jaws, which compress a preform located at their center. Formed in the present example are six pressing tools 25, 30, which are arranged in a rotationally symmetric manner about the axis of rotation, in order to avoid imbalances.

In the present example, the pressing tools 25, 30 are configured such that they carry out a compression step from the time of receiving the workpiece until they transfer it to a next processing drum or to a removal unit. As a result, the compression step can be carried out over a period while the workpiece, i.e. the preform, is being moved in the conveying direction. At the same time, another pressing tool is prepared for receiving a following first preform.

The process can proceed continuously without there being a loss of processing time during the compression for the individual preform, thereby achieving good processing quality.

The transfer wheel 7 is likewise mounted so as to be rotatable about a horizontal axis of rotation, and is located between the two processing drums. The transfer wheel 7 has a total of twelve receiving grippers 12, which are arranged radially and likewise define an effective radius 21 with their receiving nests 11. During operation, a transfer region 18 is formed between the effective radius 21 of the transfer wheel 7 and the effective radius 20 of the first processing drum. At a tangent to the radius 20 of the processing drum within this transfer region 18, the transfer of the workpiece from the first processing drum to the transfer wheel 7 takes place.

In a manner corresponding to the lower number of tools at the second processing drum 4, the transfer region 19 between the transfer wheel 7 and the second processing drum 4 is designed differently.

By way of a corresponding curve guide (not shown in FIGS. 3*a* and 3*b*), the receiving gripper can optimally cover the corresponding transfer regions 18, 19 during its radial movement of the transfer wheel.

Thus, it is possible for example with the aid of the guide curves to ensure an identical turning speed between the receiving gripper 12 and processing tool during a particular time window in which the transfer can take place.

Figure 3B:
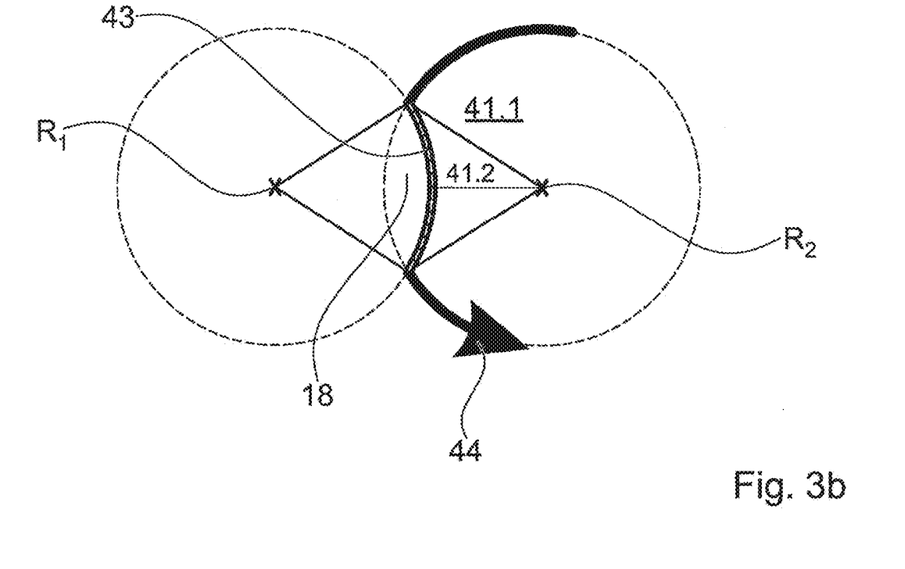
FIG. 3b schematically shows a transfer region.

This concept is illustrated once more schematically as an example in FIG. 3*b*. A first rotation radius about the axis of rotation R1 of a processing drum is illustrated on the left. This radius overlaps a second rotation radius about the axis of rotation R2 of a transfer wheel. As a result, the transfer region 18 arises, in which the tools of the processing drum continue to follow their rotation radius, but the rotation radius of the transfer wheel follows a curve 43 that deviates from the rotation curve 44.

This is allowed by the degrees of freedom of the receiving grippers and the guidance along the guide curves, as explained above. Thus, a first curve radius 41.1 of a receiving gripper is adapted dynamically to the rotation radius of the processing drum, and the workpiece is transferred at a second curve radius 41.2 at a tangent to the rotation radius of the processing drum.

Figure 4:
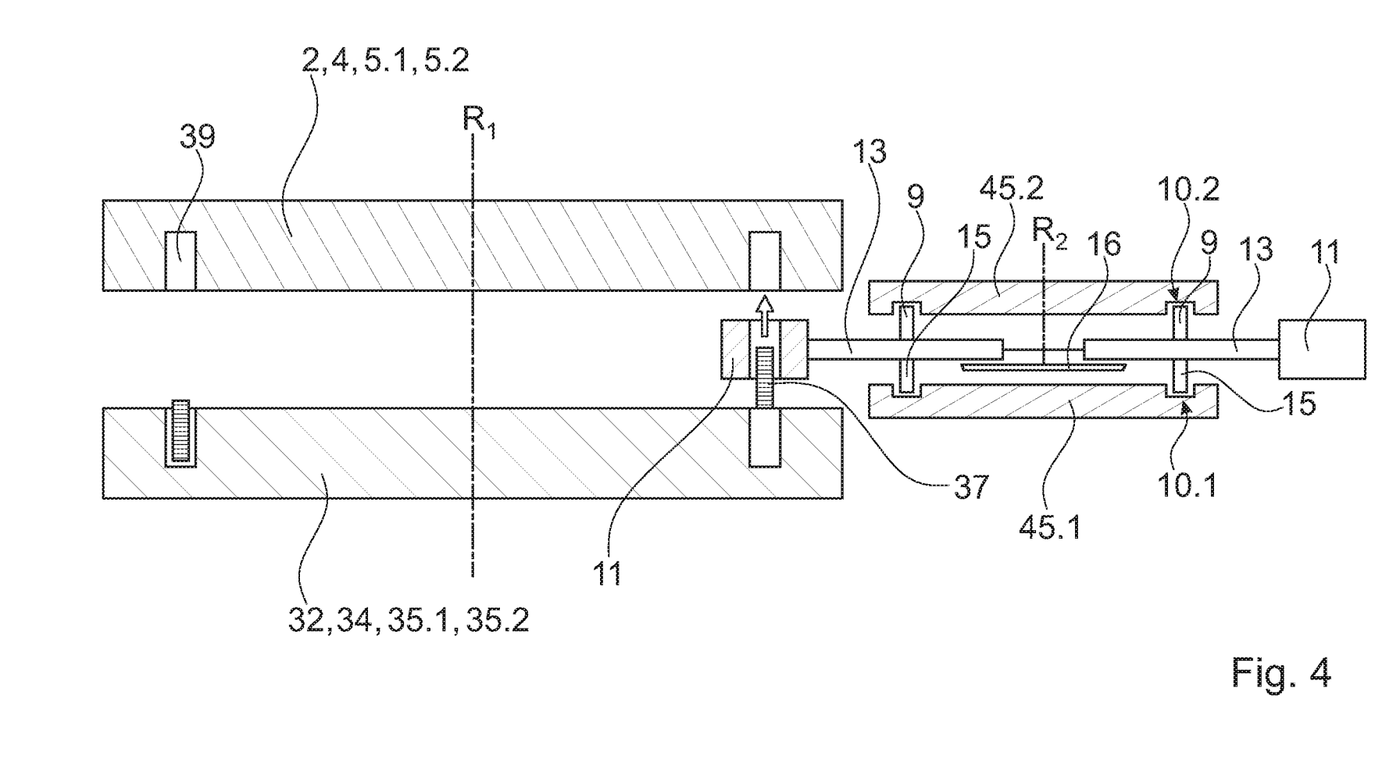
FIG. 4 schematically shows the engagement of a transfer wheel in a cross section through the axis of rotation of a processing drum.

FIG. 4 shows the transfer in more detail using the example of any desired processing drum 2, 4, 5.1, 5.2 that has an associated ejection drum 32, 34, 35.1, 35.2, which is mounted so as to be rotatable about the same axis of rotation R1.

The processing drum 2, 4, 5.1, 5.2 is shown in cross section, wherein two tools 39 are illustrated in each case schematically at radially opposite encircling radii. These tools 39 serve to receive the workpiece or preform. The tools 39 can also be responsible for a particular processing step. Thus, a tool of a processing station can be configured for example as a winding tool, as a pressing tool or as a head forming/smoothing tool.

With regard to the ejection drum 32, 34, 35.1, 35.2, the processing drum 2, 4, 5.1, 5.2 defines a gap through which a receiving gripper of a transfer wheel can engage in a transfer region that is located between the processing drum and the ejection drum, specifically coaxially between an ejection push rod 37 and the tool 39. The processing drums 2, 4, 5.1, 5.2 are shown by way of example with associated ejection drums 32, 34, 35.1, 35.2 in FIG. 4. In practice and in a specific configuration of an apparatus according to the invention, a processing drum 2, 4, 5.1, 5.2 can have permanently associated ejection drums 32, 34, 35.1, 35.2 which are adapted to the structural and functional properties of the processing drum 2, 4, 5.1, 5.2, for example with regard to the number of tools, the rotational speed, the geometry. Thus, it is possible for example for a second processing drum 4 that is provided for compressing the preforms and has a total of six tools, i.e. pressing tools, to have a correspondingly designed ejection drum 34 having six ejection push rods 37 and a corresponding guide element for guiding these ejection push rods.

During transfer, a receiving nest 11 is arranged in this intermediate space such that a receiving chamber defined by the receiving nest 11 is coaxial with the ejection push rod 37. This ejection push rod 37 can be guided three-dimensionally on the ejection drum 32, 34, 35.1, 35.2 such that it projects into the transfer region, synchronously in the transfer region with the coaxial arrangement of the receiving nest 11, such that it transports the workpiece from the receiving nest into the tool 39 in the arrow direction.

In order to equalize the speed between the transfer wheel and the processing drum or ejection drum at the time of the transfer, the transfer wheel is provided with cams 9, 15, which each act in a corresponding slot in a guide curve 10.1, 10.2 and by way of which the displaceably mounted guide rods 13 follow the movement profile of the curve. In this case, the guide rods 13 are mounted so as to be rotatable about an axis of rotation R2 via a hub 16. The guide curves 10.1, 10.2 are formed in the present example as slots on two guide discs 45.1, 45.2 that are arranged opposite and parallel to one another. The guide discs 45.1, 45.2 are fixed with respect to the hub 16. The guide curves 10.1, 10.2 thus form guide elements, which control the curve movement of the receiving grippers. The receiving grippers are additionally mounted in a rotatable manner on the hub 16, such that they can execute a pivoting movement perpendicular to the plane of the paper.

Figure 5:
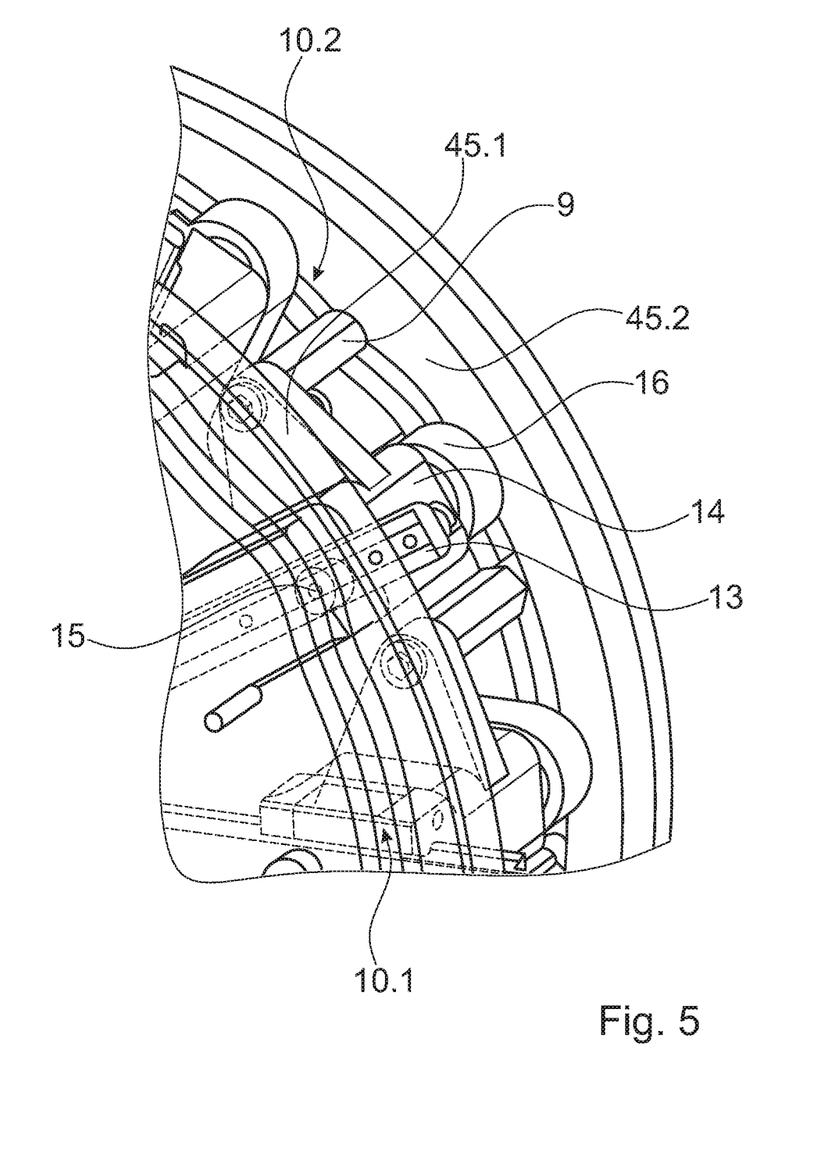
FIG. 5 shows a detail of a radius of a transfer wheel according to the invention.

FIG. 5 schematically illustrates the structure of a transfer wheel with mounted receiving grippers in a detail view. Two guide discs 45.1, 45.2 are arranged in parallel, such that they have a front side facing one another. On the respective front sides, the guide curves 10.1, 10.2 are configured as slots. Engagement means 9, 15 of the receiving grippers engage in each case in the slots of the guide curves 10.1, 10.2, wherein the receiving grippers are illustrated without receiving nests in the present illustration, in order not to impede the view into the intermediate space between the guide discs 45.1, 45.2.

The guide bushing 14 is operatively connected to the remote second guide curve 10.2 via a second cam 9 as engagement means, such that it is guided on the guide bushing 14 during the rotary movement about the axis of rotation R2 of the transfer wheel as with a guide element. The guide bushing 14 is furthermore mounted in a pivotable manner via a radial bearing with the hub 16. The hub 16 is configured in the present case as a transport wheel, which has radially arranged bearings for operatively connecting to the guide bushings 14.

Via the guide bushing 14, the guide rod 13 is mounted in a linear manner. The guide rod 13 has a cam 15, which extends in an analogous manner into the first guide curve 10.1 configured as a slot, and enters into a guided operative connection therewith.

Rotors can be attached to the cams 9, 15 in order to minimize the friction with the slots of the guide curves 10.1, 10.2.

The present invention provides an apparatus which allows continuous and scalable tampon forming, which has a number of advantages compared with known systems. Further advantageous embodiments, which can be supplemented with further features from the general description, will become apparent to a person skilled in the art from these specific exemplary embodiments.

The invention claimed is:

1. An apparatus for forming tampons, comprising:
   a. a plurality of processing drums for forming a tampon from band-form material, and
   b. at least one transfer station for continuously transferring a preform from a first processing drum to a second processing drum,
      wherein the at least one transfer station is a transfer wheel for continuously transferring the preform from the first processing drum to the second processing drum,
      wherein the transfer wheel is mounted so as to be rotatable about an axis of rotation,
      wherein the axis of rotation is parallel to an axis of rotation of the processing drums, and
      wherein the transfer wheel has radially arranged receiving grippers comprising:
         a. a receiving nest for receiving a tampon or a preform;
         b. a guide rod on which the receiving nest is arranged; and
         c. a guide bushing by way of which the guide rod is mounted so as to be displaceable along its longitudinal axis, and which is mounted on a rotatable hub.

2. The apparatus according to claim 1, wherein the first processing drum is configured for winding the band-form material to form a first preform.

3. The apparatus according to claim 2, wherein the second processing drum is configured for pressing the first preform to form a second preform.

4. The apparatus according to claim 3, wherein the plurality of processing drums comprises at least one third processing drum for forming and/or smoothing a tampon head on the second preform.

5. The apparatus according to claim 1, wherein the receiving grippers are designed such that the receiving grippers engage in a transfer region at a rotation radius of at least one of the processing drums.

6. The apparatus according to claim 5, wherein the transfer wheel has at least one guide curve that guides the receiving gripper in a radial movement such that, during a rotation of the transfer wheel relative to a processing drum, a transfer region is defined, in which a receiving nest of a receiving gripper is substantially coaxial with a processing tool of a processing drum.

7. The apparatus according to claim 5, wherein the transfer wheel comprises two guide discs, on each of which there is formed a guide curve, by way of which the receiving grippers are guided in a radial movement about the axis of rotation of the transfer wheel such that an effective radius of the receiving gripper follows a rotation radius of a processing tool and transfer takes place at a tangent to the rotation radius of the processing drum.

8. The apparatus according to claim 6, wherein the processing drums comprise an ejection drum, which is arranged so as to be rotatable about the same axis as the associated processing drum.

9. The apparatus according to claim 8,
   wherein the associated processing drum comprises a plurality of processing tools; and
   wherein the ejection drum comprises a plurality of ejection push rods that are arranged at a radius on the ejection drum such that they are arranged coaxially with the processing tools of the associated processing drum.

10. A method for forming a tampon from band-form material using the apparatus according to claim 1, comprising the steps of:
    a. providing a band-form material; and
    b. incrementally forming the band-form material via a plurality of rotating processing drums,
       wherein transfer from a first processing drum to a second processing drum takes place continuously by means of a transfer wheel.

11. The method according to claim 10, wherein the incremental forming of the band-form material comprises a winding step, a pressing step and a forming and/or smoothing step, and wherein each of these steps takes place on a particular, continuously rotating processing drum.

12. The method according to claim 11, wherein the processing drums move a workpiece in a conveying direction in each incremental forming step.

13. The method according to claim 10, wherein, during the transfer from a first processing drum to a second processing drum, the transfer wheel executes the following steps of:

a. engaging with a receiving gripper in a transfer region of a first processing drum, such that a receiving nest of the receiving gripper is located in a coaxial arrangement with a tool, and
b. ejecting a workpiece from the tool into the receiving nest, or from the receiving nest into the tool by displacing an ejection push rod in the longitudinal direction of the tool or receiving nest.

14. The method according to claim 13, wherein, in step b), the ejection push rod is arranged on an ejection drum.

15. The method according to claim 13, wherein a receiving gripper of the transfer wheel is guided, during the rotation of the transfer wheel, over a guide curve, such that there is the same speed in a transfer region between the processing drum and the receiving nest.

16. A method of using a transfer wheel comprising:
providing the transfer wheel, wherein the transfer wheel has radially circumferentially arranged receiving grippers,
using the transfer wheel for the continuous transfer of a preform from a first processing drum to a second processing drum of an apparatus for producing tampons or preforms according to the method of claim 10.

* * * * *